(12) United States Patent
Lee et al.

(10) Patent No.: US 11,999,217 B2
(45) Date of Patent: Jun. 4, 2024

(54) AIR CONDITIONING ASSEMBLY OF VEHICLE SEAT

(71) Applicant: HYUNDAI TRANSYS INCORPORATED, Seosan-si (KR)

(72) Inventors: Hwa Jun Lee, Hwaseong-si (KR); Sun Woo Kim, Hwaseong-si (KR); Ho Sub Lim, Hwaseong-si (KR)

(73) Assignee: HYUNDAI TRANSYS INCORPORATED, Seosan-si (KR)

( * ) Notice: Subject to any disclaimer, the term of this patent is extended or adjusted under 35 U.S.C. 154(b) by 272 days.

(21) Appl. No.: 17/577,860

(22) Filed: Jan. 18, 2022

(65) Prior Publication Data

US 2022/0258561 A1     Aug. 18, 2022

(30) Foreign Application Priority Data

Feb. 17, 2021   (KR) .................... 10-2021-0021170

(51) Int. Cl.
*B60H 1/00*     (2006.01)

(52) U.S. Cl.
CPC ..... *B60H 1/00285* (2013.01); *B60H 1/00028* (2013.01); *B60H 1/00564* (2013.01); *B60H 2001/00078* (2013.01)

(58) Field of Classification Search
CPC ............ B60H 1/00285; B60H 1/00028; B60H 1/00564; B60H 2001/00078
See application file for complete search history.

(56) References Cited

U.S. PATENT DOCUMENTS

| | | | | | |
|---|---|---|---|---|---|
| 4,422,824 | A | * | 12/1983 | Eisenhardt, Jr. | F04D 25/088 55/467 |
| 5,057,128 | A | * | 10/1991 | Panzica | B01D 53/0415 96/123 |
| 5,238,473 | A | * | 8/1993 | Femiani | B01D 46/10 55/400 |
| 5,265,348 | A | * | 11/1993 | Fleishman | A45D 20/12 15/300.1 |
| 5,399,120 | A | * | 3/1995 | Burns | B60H 1/00685 454/126 |
| 5,514,197 | A | * | 5/1996 | Den | F24F 8/10 55/501 |
| 5,560,835 | A | * | 10/1996 | Williams | B01D 46/22 210/791 |

(Continued)

FOREIGN PATENT DOCUMENTS

| | | |
|---|---|---|
| CN | 1839060 A | 9/2006 |
| CN | 103568784 A | 2/2014 |

(Continued)

*Primary Examiner* — David R Dunn
*Assistant Examiner* — Christopher E Veraa
(74) *Attorney, Agent, or Firm* — Bridgeway IP Law Group, PLLC; Jihun Kim

(57) ABSTRACT

Proposed is an air conditioning assembly of a vehicle seat. The air conditioning assembly includes a housing provided in a vehicle seat, in which air flows in an internal space of the housing and the air is discharged to a seating surface of the seat, and an air cleaner provided in the internal space of the housing and configured to selectively sterilize or deodorize the air flowing in the internal space of the housing by rotating according to an air conditioning mode.

9 Claims, 7 Drawing Sheets

(56) References Cited

U.S. PATENT DOCUMENTS

| | | | | |
|---|---|---|---|---|
| 5,795,131 | A * | 8/1998 | Crowhurst | F04D 29/703 55/DIG. 39 |
| 5,879,230 | A * | 3/1999 | Wardlaw | B60H 3/0608 55/467 |
| 6,099,608 | A * | 8/2000 | Harms | F24F 8/158 55/471 |
| 6,099,609 | A * | 8/2000 | Lira | F04D 29/281 55/467 |
| 6,277,176 | B1 * | 8/2001 | Tang | F04D 29/388 55/467 |
| 6,348,086 | B1 * | 2/2002 | Harms | B01D 46/0045 55/438 |
| 6,790,004 | B2 * | 9/2004 | Steinheiser | F04D 29/703 416/65 |
| 7,052,524 | B1 * | 5/2006 | Venezzio, Jr. | B01D 46/521 422/123 |
| 7,104,755 | B2 * | 9/2006 | Owens | F04D 29/701 416/62 |
| 7,674,305 | B2 * | 3/2010 | Lillquist | B01D 45/14 55/467 |
| 7,833,303 | B1 * | 11/2010 | Higgins | B01D 45/14 55/330 |
| 2006/0138812 | A1 * | 6/2006 | Aoki | B60N 2/5635 297/180.14 |
| 2012/0128539 | A1 * | 5/2012 | Gross | F24F 8/192 422/121 |
| 2013/0305930 | A1 * | 11/2013 | Oh | F02M 35/02425 96/385 |
| 2016/0273554 | A1 * | 9/2016 | Kim | B60H 1/00521 |
| 2017/0217284 | A1 * | 8/2017 | Ji | B60H 1/00457 |
| 2020/0406709 | A1 * | 12/2020 | Barbier | B60H 1/00028 |
| 2022/0071106 | A1 * | 3/2022 | Megerson | A01G 9/24 |

FOREIGN PATENT DOCUMENTS

| | | |
|---|---|---|
| CN | 105473360 A | 4/2016 |
| JP | 08-007302 Y2 | 3/1996 |
| JP | 2001-171343 A | 6/2001 |
| JP | 2007-126047 A | 5/2007 |
| KR | 10-2010-0010265 A | 2/2010 |

* cited by examiner

AIR CONDITIONING ASSEMBLY OF VEHICLE SEAT

CROSS REFERENCE TO RELATED APPLICATION

The present application claims priority to Korean Patent Application No. 10-2021-0021170, filed Feb. 17, 2021, the entire contents of which is incorporated herein for all purposes by this reference.

BACKGROUND OF THE INVENTION

Field of the Invention

The present invention relates to an air conditioning assembly of a vehicle seat, which is provided in a vehicle seat, and discharges air to a seating surface of the seat while selectively sterilizing or deodorizing the air according to an air conditioning mode before discharging the air.

Description of the Related Art

Conventionally, air conditioners and heaters are used for internal air conditioning of vehicles, and furthermore, ventilated seats for the convenience of individual passengers are widely used. The ventilated seat serves to cool the heat in the part where the seat and the passenger come into direct contact by discharging air from the seating surface of the seat.

Meanwhile, when the air inside a vehicle is polluted due to the passengers' use of the vehicle or due to the generation of microorganisms, nitrogen oxides, soot, fine dust, or odors, etc. caused by the vehicle's indoor and outdoor environmental factors, the air pollution adversely affects passengers, and thus, the importance of technology related to air cleaning inside a vehicle is increasing recently.

To solve this problem, a filter for air purification can be installed inside the ventilated seat, but due to the nature of the ventilated seat, which must be operated with low power and low noise, the type of filter used, the amount of filtering, the location of the filter, etc. are inevitably limited. Therefore, it is necessary to develop a seat air conditioning system that minimizes the above problems and has high air cleaning efficiency.

The foregoing is intended merely to aid in the understanding of the background of the present invention, and is not intended to mean that the present invention falls within the purview of the related art that is already known to those skilled in the art.

SUMMARY OF THE INVENTION

Accordingly, the present invention has been made keeping in mind the above problems occurring in the related art, and the present invention is intended to provide an air conditioning assembly of a vehicle seat configured to be provided in a seat, to discharge air to a seating surface of the seat, and to have an air cleaner that selectively sterilizes or deodorizes the air according to an air conditioning mode by using a photocatalyst.

In order to achieve the above objective, according to one aspect of the present invention, there is provided an air conditioning assembly of a vehicle seat, including: a housing provided in a seat, in which air flows in an internal space thereof and the air is discharged to a seating surface of the seat; and an air cleaner provided in the internal space of the housing and configured to selectively sterilize or deodorize the air flowing in the internal space of the housing by rotating according to an air conditioning mode.

The air conditioning assembly of a vehicle seat may further include an operating part provided on one side of the housing and configured to operate when switching to the air conditioning mode, thereby rotating the air cleaner.

The air conditioning mode may include a a ventilation mode and an air purification mode, and the air cleaner may sterilize or deodorize the air flowing in the internal space of the housing in the air purification mode.

A contact area of the air cleaner with air flowing in the internal space of the housing may change according to the air conditioning mode, and the contact area with air in the air purification mode may be larger than the contact area with air in the ventilation mode.

The housing changes an amount of air discharged to the seating surface of the seat according to the air conditioning mode, and the amount of air discharged in the air purification mode may be smaller than the amount of air discharged in the ventilation mode.

The air conditioning assembly of a vehicle seat may further include a light source provided in the internal space of the housing and configured to radiate light toward the air cleaner from a point adjacent to the air cleaner.

The air cleaner may be coated with a material containing a photocatalyst, and sterilize or deodorize the air by the light radiated from the light source reaching the photocatalyst.

The housing includes expansion portion formed in the internal space in a shape in which a flow path expands and contracts along a air flow direction, with the air cleaner being provided in the expansion portion.

A plurality of blocking parts may be provided on one side of the expansion portion in a width direction of the expansion portion and configured to block a part of the expansion portion, with the air cleaner being disposed between the plurality of blocking parts.

A discharge port may be provided at an end of the housing, and the discharge port being configured to discharge the air that has passed through the air cleaner in the internal space of the housing to the seating surface of the seat.

The discharge port may be made of an elastic body or formed in a corrugated tube shape, and and may be extended or reduced depending on a position of the seating surface of the seat.

The air conditioning assembly of a vehicle seat according to the present invention is configured to be provided in a seat, to discharge the air to a seating surface of the seat, and to have an air cleaner that selectively sterilizes or deodorizes the air according to an air conditioning mode by using a photocatalyst, thereby performing efficient seat air conditioning.

BRIEF DESCRIPTION OF THE DRAWINGS

The above and other objectives, features, and other advantages of the present invention will be more clearly understood from the following detailed description when taken in conjunction with the accompanying drawings, in which.

DETAILED DESCRIPTION OF THE INVENTION

Figure 1:
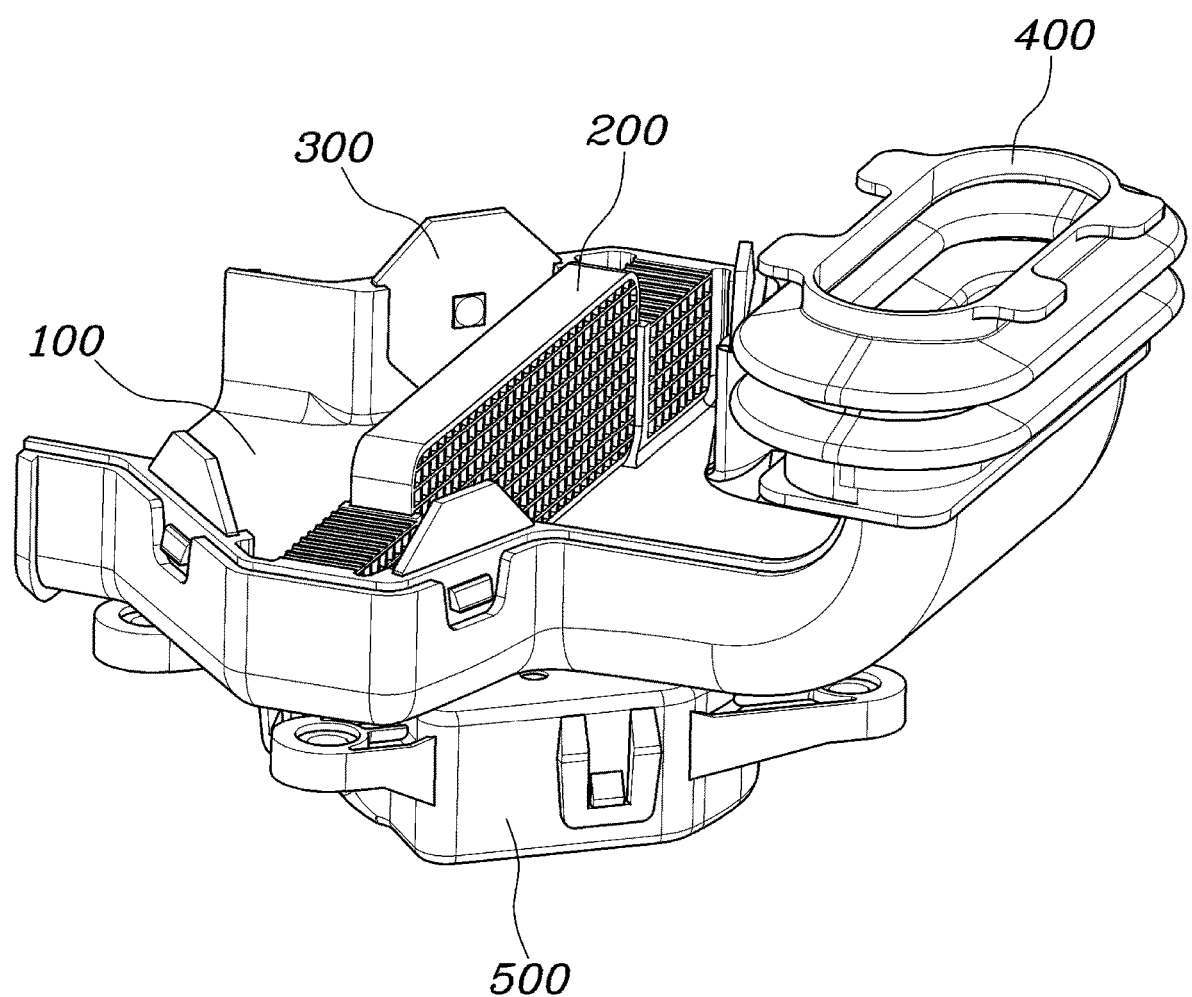
FIG. 1 is a view illustrating an air conditioning assembly of a vehicle seat according to an embodiment of the present invention.

FIG. 1 is a view illustrating an air conditioning assembly of a vehicle seat according to an embodiment of the present invention. FIGS. 2A to 4B are views illustrating that, in the air conditioning assembly of a vehicle seat according to an embodiment of the present invention, an air cleaner has a different axis of rotation and is rotated according to an air conditioning mode. FIGS. 2A to 4B mean that the axis of rotation of the air cleaner 200 may be changed according to the position of an actuator, namely, an operating part 500 or the connection structure between other components.

An air conditioning assembly of a vehicle seat, according to an embodiment of the present invention, includes: a housing 100 provided in a seat, in which air flows in an internal space thereof and the air is discharged to a seating surface of the seat; and an air cleaner 200 provided in the internal space of the housing 100 and configured to selectively sterilize or deodorize the air flowing in the internal space of the housing 100 by rotating according to an air conditioning mode. The air conditioning assembly of a vehicle seat, according to an embodiment of the present invention, may further include an operating part 500 provided on one side of the housing 100 and configured to operate when switching to the air conditioning mode, thereby rotating the air cleaner 200.

In the case of the air conditioning assembly of a vehicle seat according to an embodiment of the present invention, the air discharged to a seat seating surface through the housing 100 is sterilized or deodorized by the air cleaner 200 and discharged, however, the air cleaner 200 selectively sterilizes or deodorizes the air discharged by rotating according to the air conditioning mode, thereby optimizing the air conditioning efficiency.

Specifically, when a passenger sits on the seat and desires a general ventilation function, the air cleaner 200 is rotated by the operating part 500 such as an actuator provided on the outer surface of the housing 100 to minimize the contact area of the air passing through the air cleaner 200 in the internal space of the housing 100, and this will increase ventilation efficiency or output. When the passenger is not seated in the seat and there is no need to have high ventilation efficiency or output, the air cleaner 200 is rotated back to its original position to maximize the contact area of the air passing through the air cleaner 200 in the internal space of the housing 100, and the air cleaner 200 performs a sterilization or deodorization function.

In the case of the air conditioning assembly of a vehicle seat according to an embodiment of the present invention, the air conditioning mode includes a ventilation mode or an air purification mode, and the air cleaner 200 may sterilize or deodorize the air flowing in the internal space in the air purification mode. That is, in the seat provided with the air conditioning assembly of a vehicle seat according to an embodiment of the present invention, a seating sensor may detect whether a passenger is seated, and when a passenger is determined to be seated, the system operates in the ventilation mode, whereas, when no passenger is determined to be seated, the system operates in the purification mode.

In other words, when a passenger is seated, the air cleaner 200 is rotated so as not to affect the ventilation performance or ventilation output in the ventilation mode to minimize the resistance when the air flows, whereas, when no passenger is seated, the air cleaner 200 is rotated again to increase the contact area of the air passing through the air cleaner 200 to maximize the sterilization or deodorization performance.

Figure 2A:
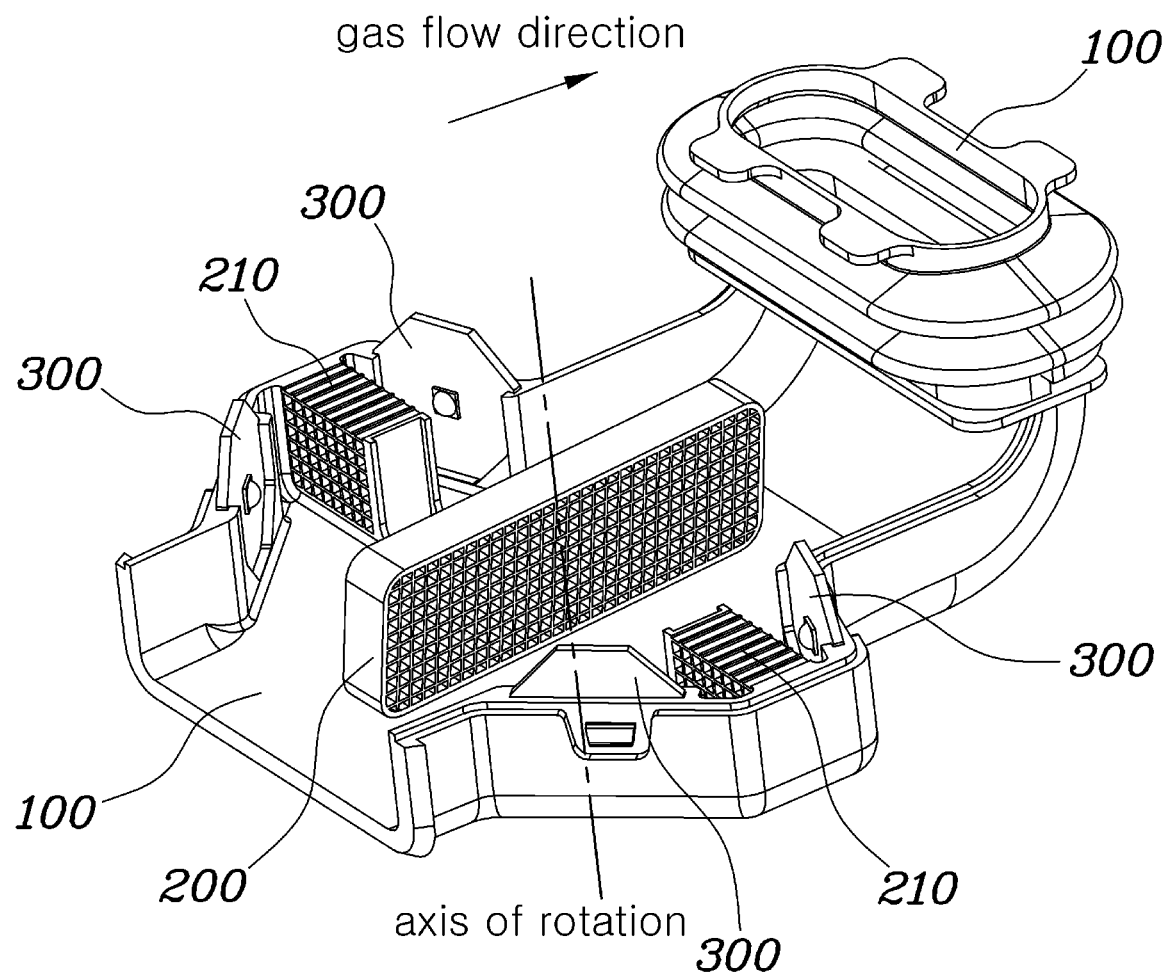
FIGS. 2A to 4B are views illustrating that, in the air conditioning assembly of a vehicle seat according to an embodiment of the present invention, an air cleaner has a different axis of rotation and is rotated according to an air conditioning mode.
Figure 2B:
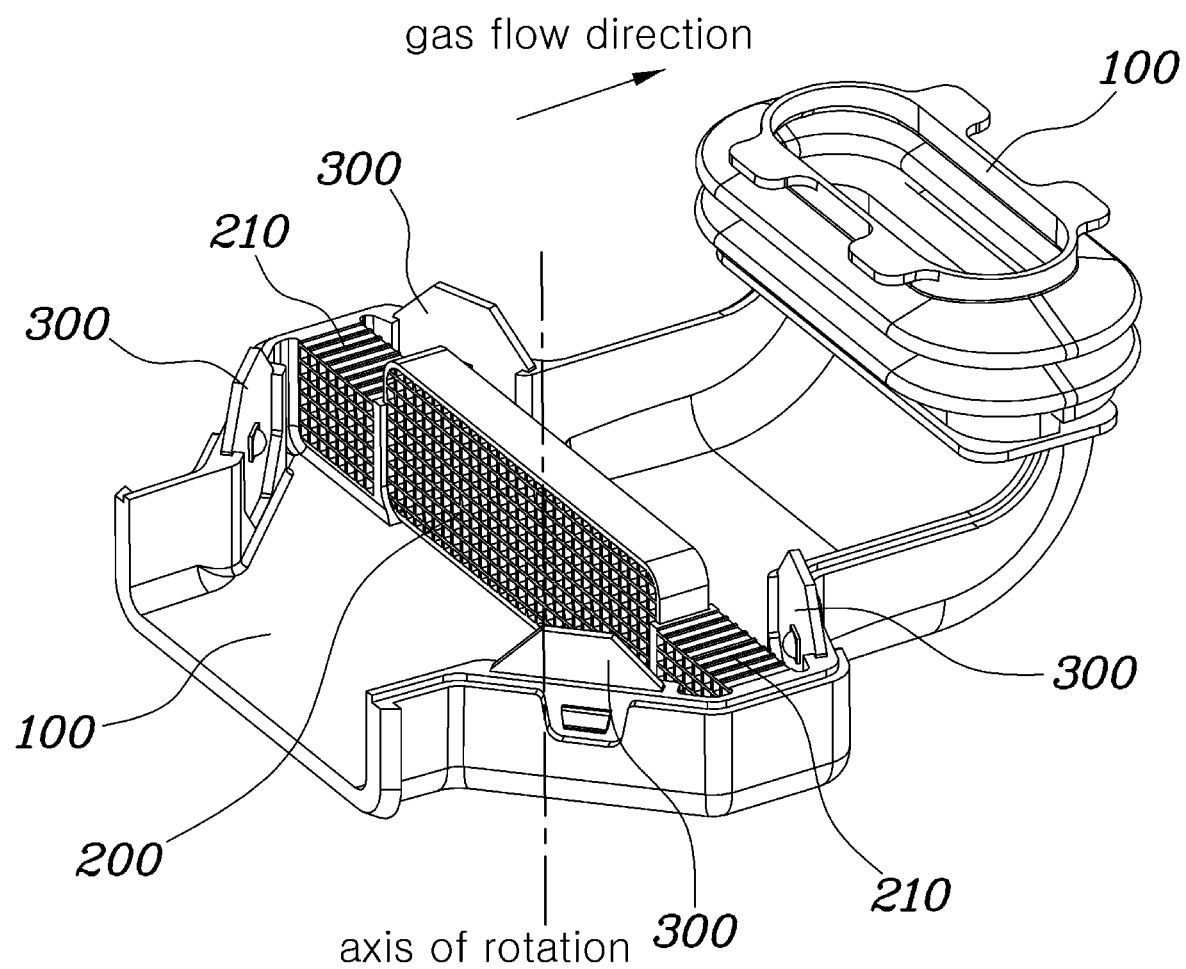
Figure 3A:
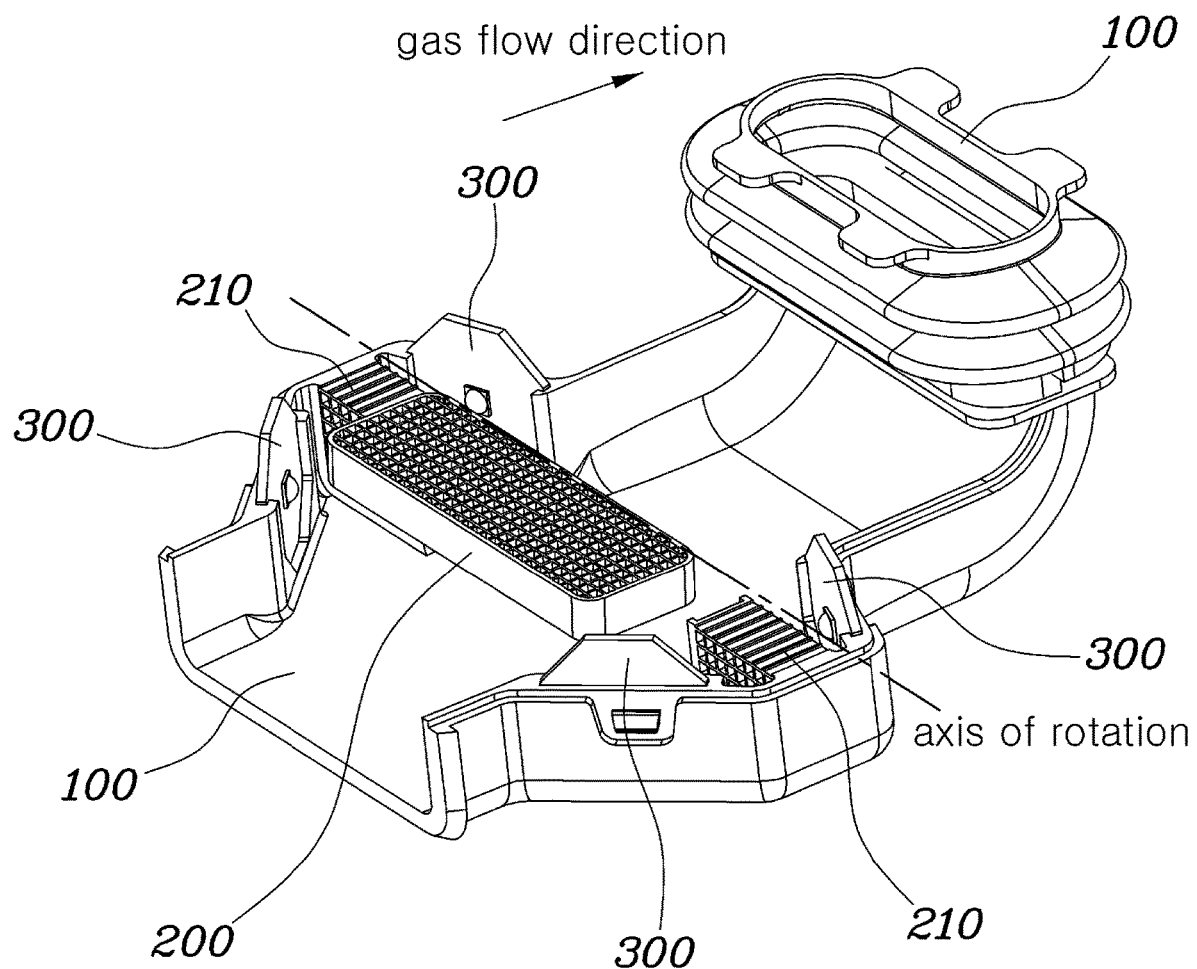
Figure 3B:
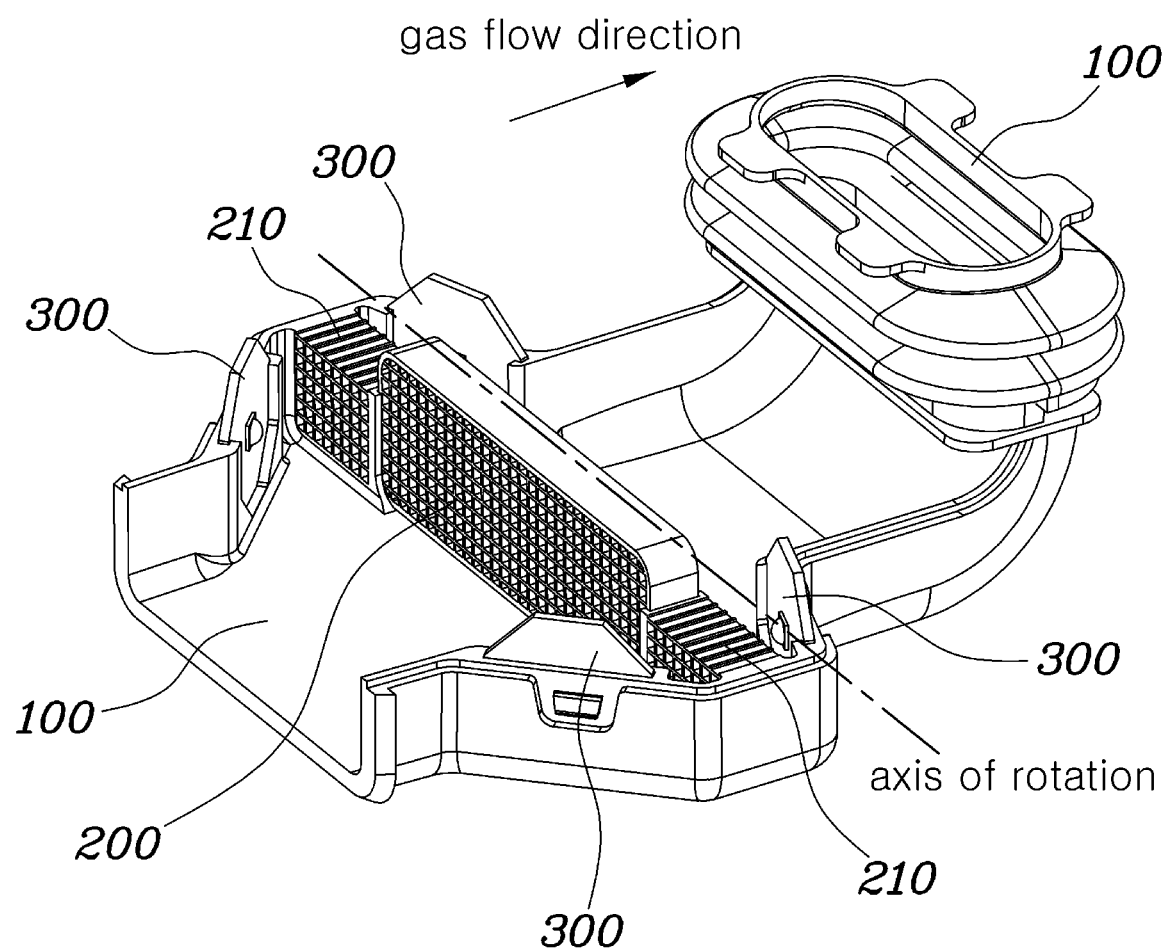
Figure 4A:
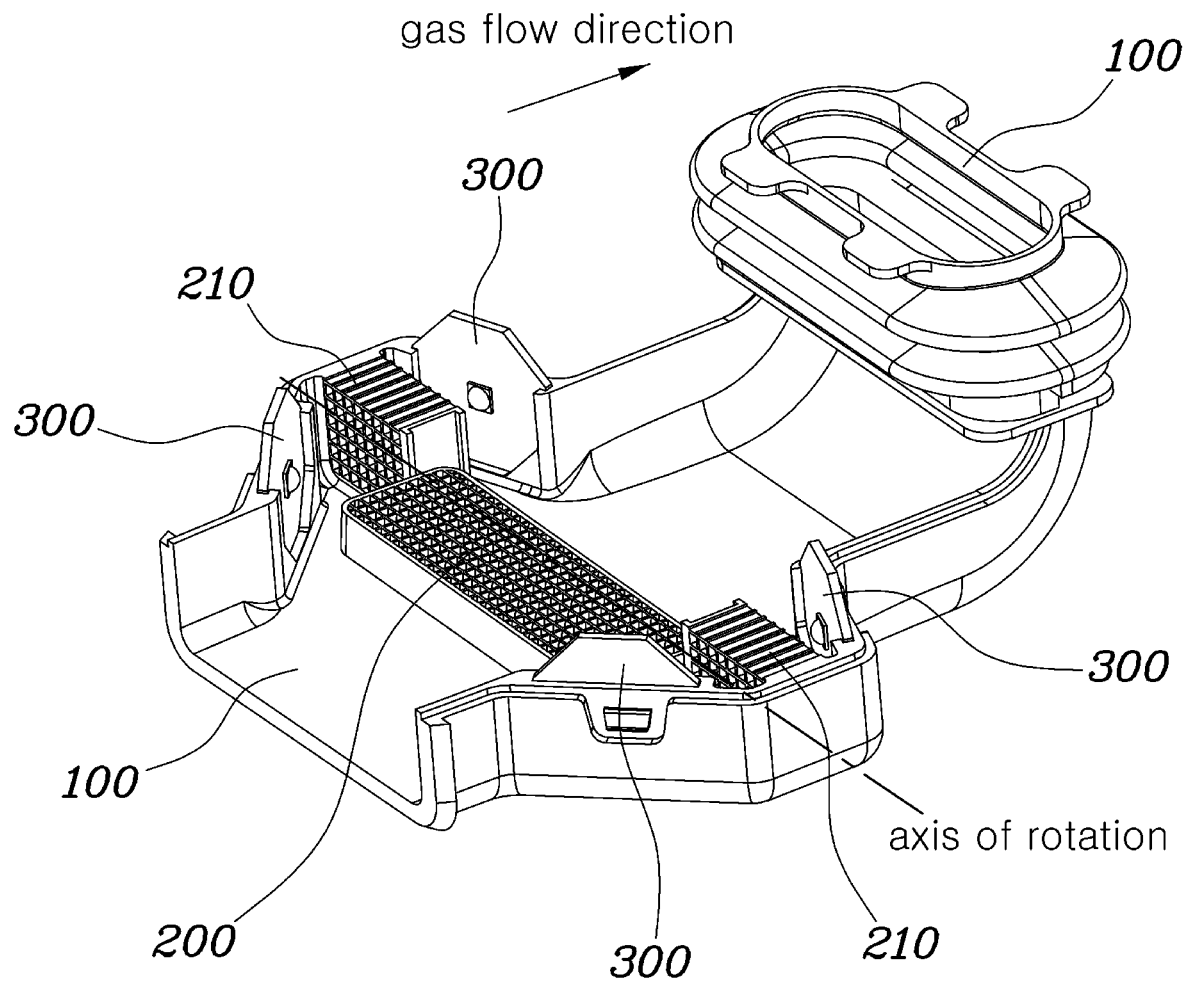
Figure 4B:
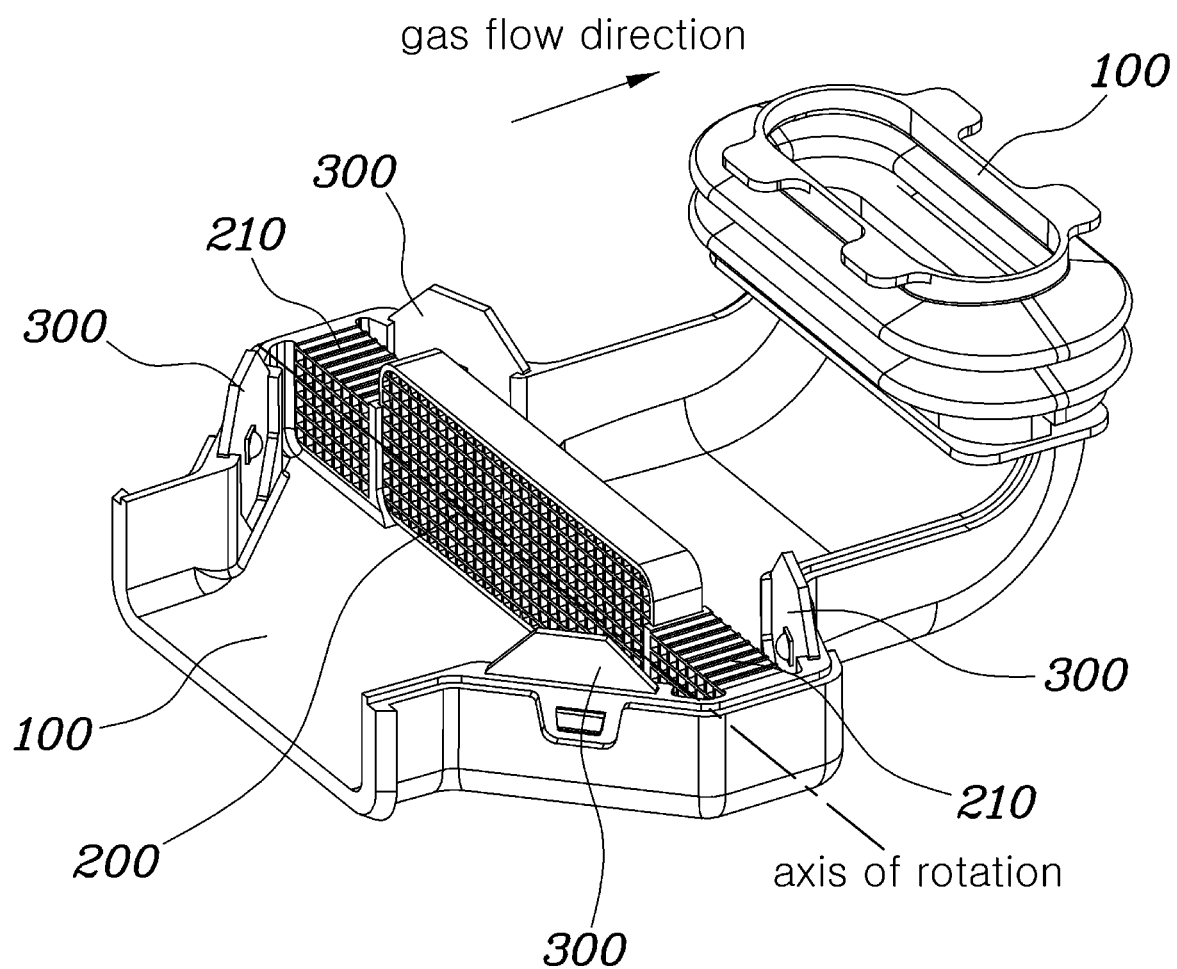

To be specific, the contact area of the air cleaner with air flowing in the internal space changes according to the air conditioning mode, and the contact area with air in the air purification mode may be larger than the contact area with air in the ventilation mode. Referring to FIGS. 2A to 4B, FIGS. 2A, 3A, and 4A show the ventilation mode, and FIGS. 2B, 3B, and 4B show the air purification mode. As shown in the drawings, in the ventilation mode, the air cleaner 200 is rotated to minimize the contact area with the air in the direction in which the air flows, thereby increasing the ventilation performance or ventilation efficiency according to the ventilation mode, whereas, in the air purification mode, the air cleaner 200 is rotated 90 degrees again to maximize the contact area with the flowing air, thereby increasing the air cleaning efficiency.

In addition, the housing 100 changes an amount of air discharged to the seating surface of the seat according to the air conditioning mode, and the amount of air discharged in the air purification mode may be smaller than the amount of air discharged in the ventilation mode. According to each air conditioning mode, the housing 100 controls the output of the blower to adjust the amount of air discharged. In other words, in the ventilation mode, resistance by the air cleaner 200 is minimized when air is discharged, and the ventilation output can be adjusted as desired by the passenger, however, in the air purification mode, the air is subjected to resistance by the rotation of the air cleaner 200, and when the flow speed of the air passing through the air cleaner 200 is fast, sterilization or deodorization cannot be sufficient. Therefore, it will be possible to increase the air cleaning efficiency through the air conditioning assembly of a vehicle seat according to an embodiment of the present invention by adjusting the discharge amount within the output limit of the blower.

Meanwhile, the air conditioning assembly of a vehicle seat, according to an embodiment of the present invention, may further include a light source 300 that is provided in the internal space of the housing and radiates light toward the air cleaner 200 from a point adjacent to the air cleaner 200. A material containing a photocatalyst is applied to the air cleaner 200, and the light radiated from the light source 300 reaches the photocatalyst to sterilize or deodorize the air.

Specifically, photocatalyst refers to a compound that absorbs light energy to initiate a photochemical reaction and promotes a photochemical reaction as a catalyst, and has a sterilizing or deodorizing effect when irradiated with light. Here, the light source 300 may be formed of an LED module, and the LED module is a device that splits light waves with a wavelength of 380 nm or less and radiates UV-A level light. Titanium oxide (TiO2) may be used as the photocatalyst. The light source 300 may be provided in plurality with a specific spectral angle (e.g., 120 degrees) to face the air cleaner 200 in the internal space of the housing 100 so that the entire photocatalytic surface of the air cleaner 200 is irradiated, increasing the air cleaning efficiency.

In addition, in the air purification mode, when the air cleaner 200 is rotated to maximize the contact area, the light source 300 may operate and radiate light to sterilize or deodorize the air passing through the air cleaner 200. Even in the ventilation mode, when the air cleaner 200 is rotated to make the contact area small, so the air cleaning efficiency may be decreased, the light source 300 may still operate and radiate light to sterilize or deodorize the air passing around the air cleaner 200.

Meanwhile, in the case of the air conditioning assembly of a vehicle seat, according to an embodiment of the present invention, in the internal space of the housing 100, an expansion portion (no reference numeral assigned) is formed in a shape in which a flow path expands and contracts along a air flow direction, and the air cleaner 200 may be provided in the expansion portion. A plurality of blocking parts 210 are provided on one side of the expansion portion in a width direction of the expansion portion and block a part of the expansion portion, and the air cleaner 200 may be disposed between the plurality of blocking parts 210.

To be specific, referring to FIGS. 2A to 4B, FIGS. 2A and 2B illustrate rotation around a vertical axis of rotation; FIGS. 3A and 3B illustrate rotation around a horizontal axis of rotation; and FIGS. 4A and 4B illustrate rotation around a horizontal central axis of rotation.

The housing 100 is formed in a structure in which the flow path at the point where the air cleaner 200 is located is expanded, thus slowing the flow speed in the air purification mode and increasing the contact area with the air to be sterilized or deodorized by using the photocatalyst, thereby increasing air cleaning efficiency. Also, the light source 300 for radiating light to the photocatalyst is located in the expansion portion, so that the light source 300 radiates light to the air cleaner 200 with a specific spectral angle to cover the entire photocatalyst surface of the air cleaner 200.

In addition, the blocking part 210 may block a part of the flow path to control the discharge amount. The blocking part 210 may be formed in the same structure as the air cleaner 200 and coated with a photocatalyst, thereby maximizing air cleaning efficiency by sterilizing or deodorizing the flowing air together with the air cleaner 200 in the air purification mode, while not affecting ventilation performance or ventilation output in the ventilation mode.

Meanwhile, in the case of the air conditioning assembly of a vehicle seat, according to an embodiment of the present invention, a discharge port 400 is provided at the end of the housing 100, and the discharge port 400 may discharge the air that has passed through the air cleaner 300 in the internal space of the housing 100 to the seating surface of the seat. The discharge port 400 may be made of an elastic body or formed in a corrugated tube shape, and and may be extended or reduced depending on a position of the seating surface of the seat.

Specifically, the discharge port 400 is a point at which ventilated air or sterilized or deodorized air is discharged from the housing 100, and is connected to the seating surface of the seat to discharge air toward the seating surface. Since the discharge port 400 is made of an elastic body or formed in a corrugated tube shape, it is possible to stably supply air to the seating surface of the seat even when the seat moves forward, backward, left and right, or when a passenger is seated, or vibration of a vehicle or impact occurs.

Although shown and described with respect to specific embodiments of the invention, it will be apparent to those skilled in the art that the present invention can be variously improved and changed without departing from the spirit of the present invention provided by the following claims.

What is claimed is:

1. An air conditioning assembly of a vehicle seat, the air conditioning assembly comprising:
   a housing disposed in a seat, the housing being configured to have air flowing in an internal space of the housing and to discharge air to a seating surface of the seat; and
   an air cleaner disposed in the internal space of the housing, the air cleaner being configured to selectively sterilize or deodorize the air flowing in the internal space of the housing and to rotate according to an air conditioning mode,
   wherein in the internal space of the housing, the housing includes an expansion portion having a shape in which a flow path expands and contracts along an air flow direction, wherein the air cleaner is disposed in the expansion portion, and
   wherein a plurality of blocking parts are disposed on one side of the expansion portion in a width direction of the expansion portion and configured to block a part of the expansion portion, wherein the air cleaner is disposed between the plurality of blocking parts.

2. The air conditioning assembly of claim 1, further comprising:
   an actuator disposed on one side of the housing, the actuator being configured to operate when switching to the air conditioning mode and thereby rotate the air cleaner.

3. The air conditioning assembly of claim 1, wherein the air conditioning mode includes a ventilation mode and an air purification mode, and the air cleaner is configured to sterilize or deodorize the air flowing in the internal space of the housing in the air purification mode.

4. The air conditioning assembly of claim 3, wherein the air cleaner is configured to change an area of the air cleaner in contact with the air flowing in the internal space of the housing according to the air conditioning mode, wherein an area in contact with the air in the air purification mode is larger than an area in contact with the air in the ventilation mode.

5. The air conditioning assembly of claim 3, wherein the housing is configured to change an amount of the air discharged to the seating surface of the seat according to the air conditioning mode, wherein an amount of the air discharged in the air purification mode is smaller than an amount of the air discharged in the ventilation mode.

6. The air conditioning assembly of claim 1, further comprising:
   a light source disposed in the internal space of the housing and configured to radiate light toward the air cleaner from a point adjacent to the air cleaner.

7. The air conditioning assembly of claim 6, wherein the air cleaner has a coating having a material containing a photocatalyst, the air cleaner being configured to sterilize or deodorize the air by the light radiated from the light source reaching the photocatalyst.

8. The air conditioning assembly of claim 1, wherein a discharge port is disposed at an end of the housing, the discharge port being configured to discharge the air that has passed through the air cleaner in the internal space of the housing to the seating surface of the seat.

9. The air conditioning assembly of claim 8, wherein the discharge port has an elastic body or a corrugated tube shape, the discharge port being configured to be extended or reduced depending on a position of the seating surface of the seat.

* * * * *